US012551230B2

(12) United States Patent
Tada et al.

(10) Patent No.: US 12,551,230 B2
(45) Date of Patent: Feb. 17, 2026

(54) MEDICAL DEVICE

(71) Applicant: TERUMO KABUSHIKI KAISHA, Tokyo (JP)

(72) Inventors: Yuichi Tada, Santa Clara, CA (US); Yoichiro Kuwano, Tokyo (JP); John Barritt, San Jose, CA (US)

(73) Assignee: TERUMO KABUSHIKI KAISHA, Tokyo (JP)

(*) Notice: Subject to any disclaimer, the term of this patent is extended or adjusted under 35 U.S.C. 154(b) by 610 days.

(21) Appl. No.: 17/747,968

(22) Filed: May 18, 2022

(65) Prior Publication Data

US 2022/0273334 A1 Sep. 1, 2022

Related U.S. Application Data

(63) Continuation of application No. PCT/JP2019/050205, filed on Dec. 20, 2019.

(51) Int. Cl.
*A61B 17/3207* (2006.01)

(52) U.S. Cl.
CPC .............................. *A61B 17/320758* (2013.01)

(58) Field of Classification Search
CPC ............................................ A61B 17/320758
See application file for complete search history.

(56) References Cited

U.S. PATENT DOCUMENTS 4,355,977 A * 10/1982 Ota .......................... A61C 1/14 433/131
5,490,860 A 2/1996 Middle et al.
5,620,415 A 4/1997 Lucey et al.
9,351,757 B2 5/2016 Kusleika
9,788,854 B2 10/2017 Simpson et al.
2010/0152761 A1* 6/2010 Mark ............. A61B 17/320758 606/180

(Continued)

FOREIGN PATENT DOCUMENTS

JP H06-269460 A 9/1994
JP 2013-146559 A 8/2013

OTHER PUBLICATIONS

English Translation of International Search Report dated Mar. 17, 2020, mailed in counterpart International Application No. PCT/JP2019/050205, 2 pages.

(Continued)

*Primary Examiner* — Erin Mcgrath
(74) *Attorney, Agent, or Firm* — Kim & Stewart LLP

(57) ABSTRACT

A medical device that removes an object in a body lumen, includes a rotatable drive shaft, an outer tube that accommodates the drive shaft and is rotatable independent of the drive shaft, a cutter attached to a distal portion of the drive shaft for cutting the object, a first housing that accommodates a proximal portion of the drive shaft and has an outer surface including a first groove that extends around a rotation axis of the drive shaft, a second housing interlocked with a proximal portion of the outer tube and rotatable around the first housing, the second housing having an inner surface that faces the outer surface and includes a second groove that extends along the rotation axis, and a moving member that fits into the first and second grooves and is movable along the first and second grooves according to rotation of the second housing.

14 Claims, 7 Drawing Sheets

(56) References Cited

U.S. PATENT DOCUMENTS

| | | | | |
|---|---|---|---|---|
| 2014/0031844 | A1* | 1/2014 | Kusleika | A61B 17/320783 606/159 |
| 2015/0305769 | A1* | 10/2015 | Ibragimov | A61M 25/0606 606/180 |
| 2017/0123131 | A1* | 5/2017 | Root | F21V 17/12 |

OTHER PUBLICATIONS

English Translation of Written Opinion dated Mar. 17, 2020, mailed in counterpart International Application No. PCT/JP2019/050205, 3 pages.

* cited by examiner

MEDICAL DEVICE

CROSS-REFERENCE TO RELATED APPLICATION(S)

This application is a continuation of International Patent Application No. PCT/JP2019/050205 filed Dec. 20, 2019, the entire contents of which are incorporated herein by reference.

BACKGROUND OF THE INVENTION

Field of the Invention

This disclosure relates to a medical device for removing an object in a body lumen.

Background Art

Examples of a treatment method for a stenosed site caused by a plaque, a thrombus, and the like in a blood vessel include a method for dilating the blood vessel by using a balloon, and a method for causing a mesh-shaped or coil-shaped stent to indwell the blood vessel as a support for the blood vessel. However, it is difficult for these methods to treat a stenosed site that is hardened by calcification or a stenosed site that is formed at a bifurcated portion in the blood vessel. Such a stenosed site is treated by a method for cutting and removing a stenotic material such as a plaque or a thrombus.

For example, there is a conventional device including a cutting portion that cuts an object in a blood vessel by rotating. This device is a rapid exchange type device in which a guide wire lumen is disposed only at a distal portion.

In such a device, when the distal portion that rotatably holds the cutting portion rotates, the guide wire tends to be entangled with a proximal portion of the device. In addition, if the device rotates too much, the device may be twisted and damaged.

SUMMARY OF THE INVENTION

One or more embodiments provide a medical device capable of limiting, within a predetermined range, a rotation amount of an outer tube rotatably covering a drive shaft that drives a cutting portion.

A medical device according to one embodiment is a medical device that removes an object in a body lumen. The medical device comprises a rotatable drive shaft, an outer tube that accommodates the drive shaft and is rotatable independent of the drive shaft, a cutter attached to a distal portion of the drive shaft and by which the object is cut, a first housing that accommodates a proximal portion of the drive shaft and has an outer surface including a first groove that extends around a rotation axis of the drive shaft, a second housing that is interlocked with a proximal portion of the outer tube and rotatable around the first housing, the second housing having an inner surface that faces the outer surface of the first housing and includes a second groove that extends along the rotation axis of the drive shaft, and a moving member that fits into the first and second grooves and is movable along the first and second grooves according to rotation of the second housing.

In the medical device configured as described above, the second housing is rotatable with respect to the first housing until the moving member reaches the end portion of the first groove or the second groove. Further, the second housing is restricted from rotating with respect to the first housing by the moving member contacting the end portion of the first groove or the end portion of the second groove. Therefore, a rotation amount of the outer tube that rotatably accommodates the drive shaft that drives the cutting portion can be limited to a predetermined range.

DESCRIPTION OF EMBODIMENTS

Figure 1:
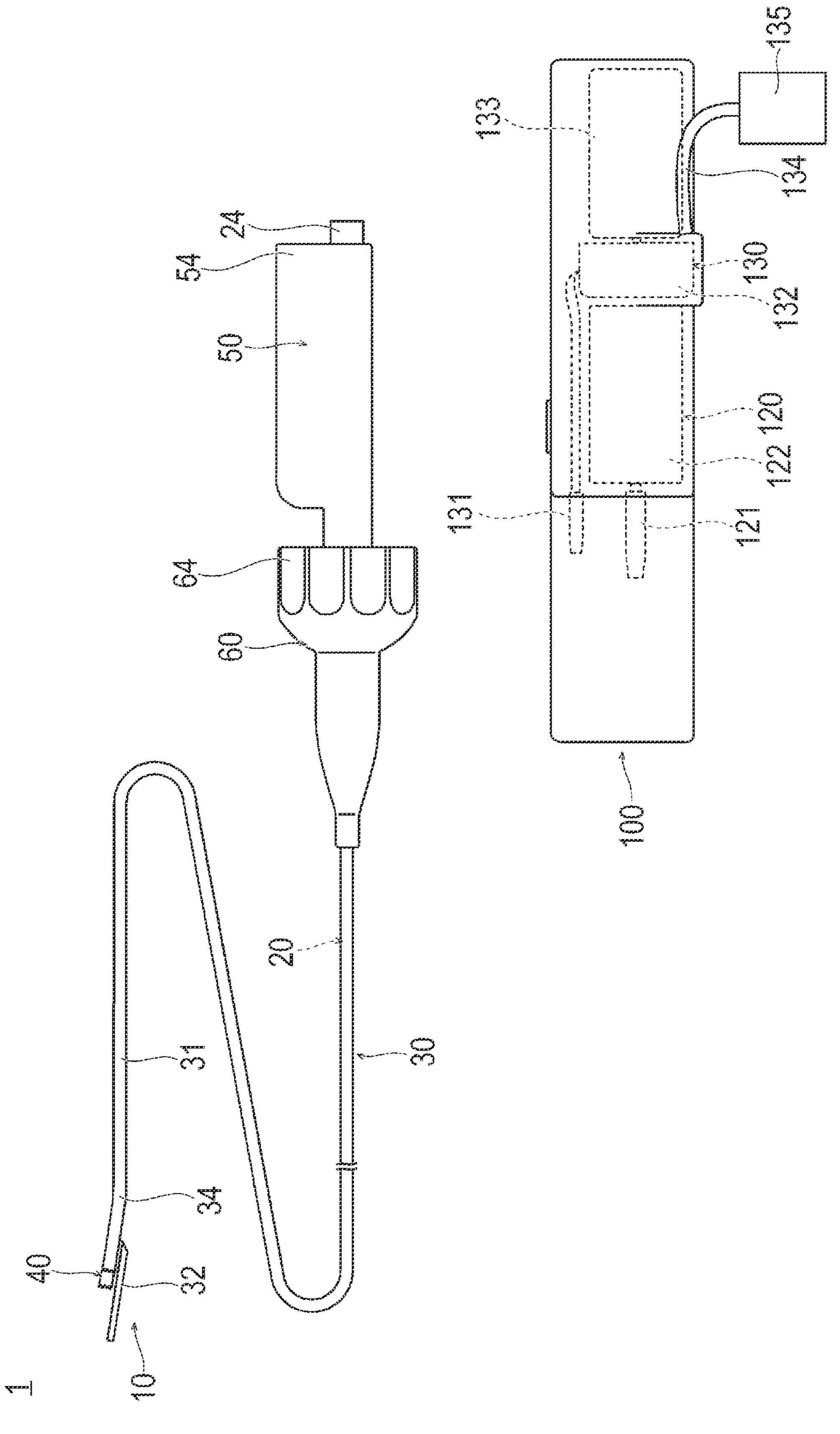
FIG. 1 is a plan view showing a medical device and a drive device according to a first embodiment.

Hereinafter, embodiments according to the disclosure will be described with reference to the drawings. A size and a ratio of each member in the drawings may be exaggerated for convenience of description and may differ from an actual size and ratio.

First Embodiment

A medical device 10 according to a first embodiment is inserted into a blood vessel in an acute lower limb ischemia or a deep vein thrombosis, and is used for a procedure for removing a thrombus, a plaque, an atheroma, a calcified lesion, and the like. In the present specification, a side of the medical device 10 to be inserted into a blood vessel is referred to as a "distal side", and the other side is referred to as a "proximal side". An object to be removed is not necessarily limited to the thrombus, the plaque, the atheroma, and the calcified lesion, and any object that may be present in a body lumen or a body-cavity may be removed.

As shown in FIG. 1, the medical device 10 is interlocked with and driven by a drive device 100 that generates a driving force. The medical device 10 and the drive device 100 make up one medical system 1.

Figure 2:
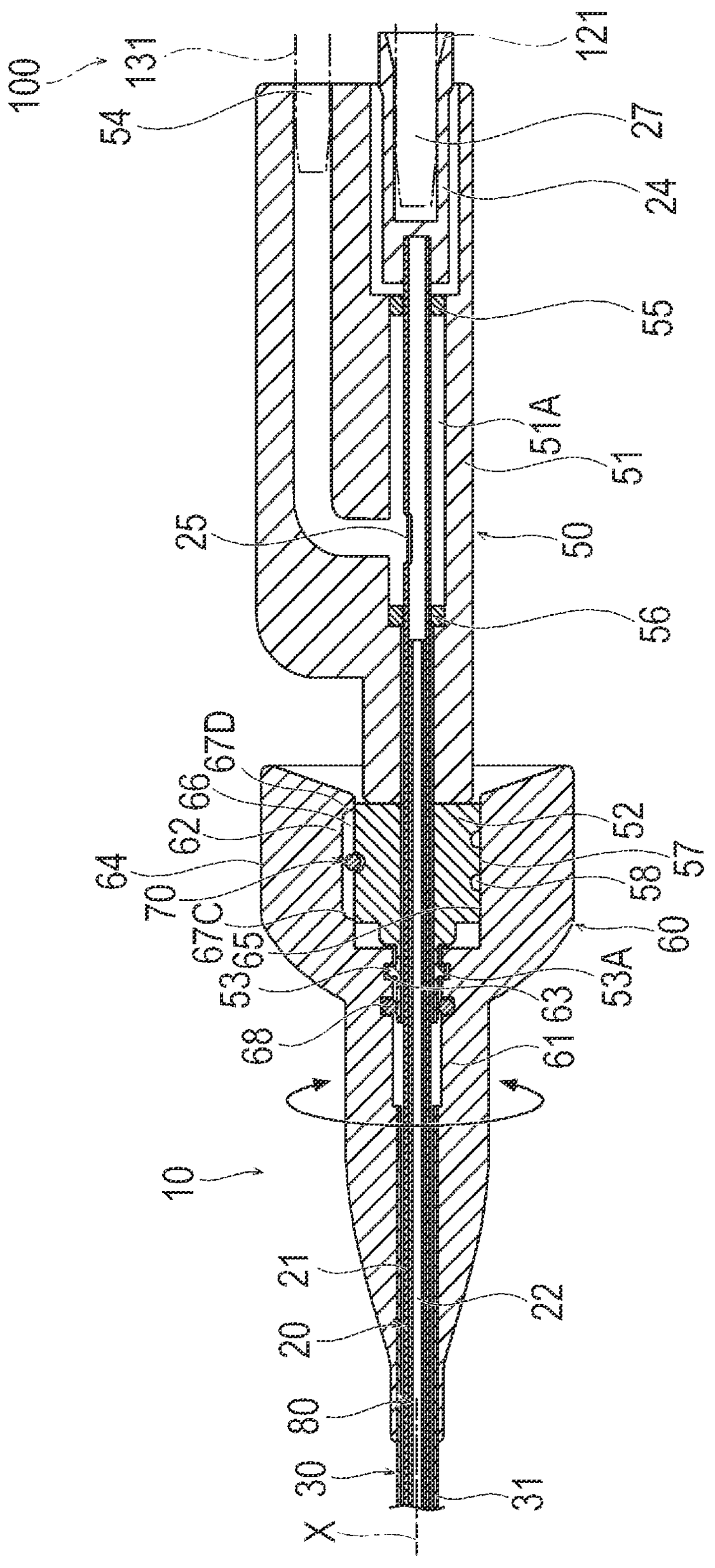
FIG. 2 is a cross-sectional view showing a proximal portion of a medical device according to a first embodiment.
Figure 3:
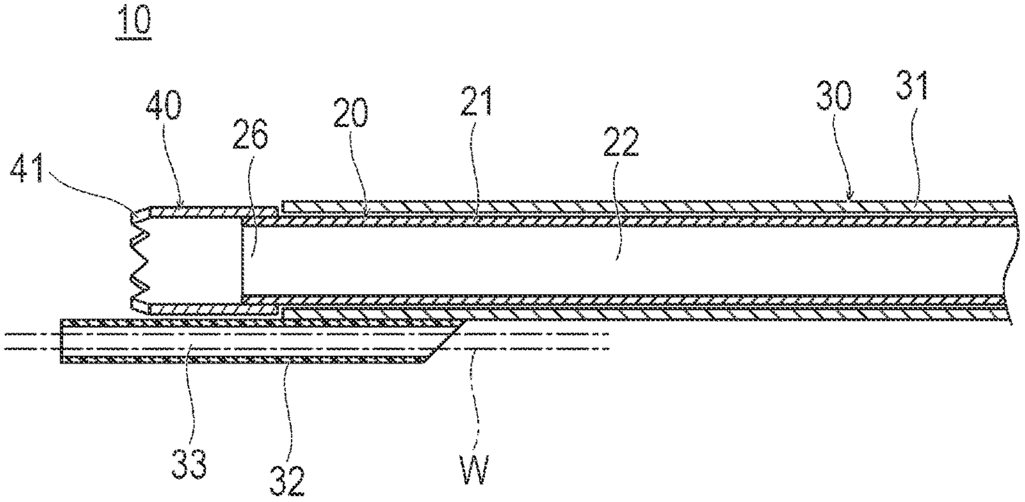
FIG. 3 is a cross-sectional view showing a distal portion of a medical device according to a first embodiment.

As shown in FIGS. 1 to 3, the medical device 10 includes a long drive shaft 20 that is rotationally driven, an outer tube 30 that accommodates the drive shaft 20, and a cutting portion 40 that cuts an object such as a thrombus. The medical device 10 further includes a first housing 50 that rotatably holds a proximal portion of the drive shaft and a second housing 60 that is interlocked with a proximal portion of the outer tube 30. The medical device 10 further includes a moving member 70 disposed between the first housing 50 and the second housing 60, and an inner tube 80 disposed inside the drive shaft 20.

The drive shaft 20 transmits a rotational force to the cutting portion 40. The drive shaft 20 includes an aspiration lumen 22 for transporting a cut object to the proximal side. The drive shaft 20 includes a long tubular drive tube 21 having an axis X and a rotary input portion 24 fixed to a proximal portion of the drive tube 21.

The drive tube 21 penetrates the outer tube 30, and the cutting portion 40 is fixed to a distal portion thereof. The proximal portion of the drive tube 21 is located inside the second housing 60. The drive tube 21 is rotationally driven by a rotary drive shaft 121, which will be described later, via the rotary input portion 24. The drive tube 21 includes, at a distal end thereof, an inlet portion 26 into which debris (e.g., a cut thrombus or the like), which is an object to be aspirated, enters. The lumen of a proximal end of the drive tube 21 is closed, and the proximal end of the drive tube 21 is fixed to the rotary input portion 24. The drive tube 21 includes, on a side surface of the proximal portion located inside the second housing 60, a lead-out portion 25 through which the aspiration lumen 22 opens. The lead-out portion 25 is an outlet from which the debris that entered an inside of the drive tube 21 from the inlet portion 26 is discharged.

The drive tube 21 is flexible and has a characteristic that a rotational power acting from the proximal side can be transmitted to the distal side. The drive tube 21 may include one member as a whole, or may include a plurality of members. The drive tube 21 may have a spiral slit or groove formed by laser processing or the like in order to adjust rigidity. In addition, the distal portion and the proximal portion of the drive tube 21 may be made of different members.

As a constituent material for the drive tube 21, for example, stainless steel, a shape memory alloy such as a nickel-titanium alloy, an alloy (e.g., silver brazing filler metal) made of silver, copper, zinc, and the like, an alloy (e.g., solder component) made of gold, tin, and the like, a cemented carbide such as tungsten carbide, polyolefins such as polyethylene and polypropylene, polyamides, polyesters such as polyethylene terephthalate, fluoropolymers such as an ethylene tetrafluoroethylene copolymer (ETFE), polyether ether ketone (PEEK), and polyimides can be preferably used. In addition, the drive tube 21 may be made of a plurality of materials, and a reinforcing member such as a wire rod may be embedded therein.

The rotary input portion 24 is a substantially cylindrical member fixed to the proximal end of the drive tube 21. The rotary input portion 24 is a member that is interlocked with the rotary drive shaft 121 of the drive device 100 to receive the rotational power. A proximal portion of the rotary input portion 24 includes a fitting recess 27 into which the rotary drive shaft 121 is fitted.

The inner tube 80 is a flexible tube body and is disposed inside the drive shaft 20. The inner tube 80 prevents an inner peripheral surface of the drive shaft 20 from being damaged due to the debris flowing inside the drive shaft 20. The inner tube 80 may or may not be fixed to the inner peripheral surface of the drive shaft 20. In one embodiment, the inner tube 80 may be omitted.

The outer tube 30 includes an outer tube main body 31 that rotatably accommodates the drive shaft 20, and a distal tube 32 that is fixed to a side surface of a distal portion of the outer tube main body 31.

The outer tube main body 31 is a tube body, and a proximal portion of the outer tube main body 31 is fixed to the second housing 60. The proximal portion of the outer tube main body 31 may be directly fixed to the second housing 60, or may be fixed to a joint 53 which is fixed to the second housing 60, thereby being indirectly fixed to the second housing 60. The distal portion of the outer tube main body 31 is located on a proximal side of the cutting portion 40. The outer tube main body 31 includes, at the distal portion, a curved portion 34 that bends at a predetermined angle. The curved portion 34 can be used for changing a direction of a distal end of the outer tube main body 31 by rotating the outer tube main body 31.

The distal tube 32 is fixed to an outer peripheral surface of the distal portion of the outer tube main body 31. The distal tube 32 has a guide wire lumen 33 into which a guide wire can be inserted. Therefore, the medical device 10 is a rapid exchange type device in which the guide wire lumen 33 is formed only at a distal portion thereof.

Constituent materials of the outer tube main body 31 and the distal tube 32 are not particularly limited. As the constituent materials thereof, for example, stainless steel, a shape memory alloy such as a nickel-titanium alloy, an alloy (e.g., silver brazing filler metal) made of titanium, silver, copper, zinc, and the like, an alloy (e.g., solder component) made of gold, tin, and the like, a cemented carbide such as tungsten carbide, polyolefins such as polyethylene and polypropylene, polyamides, polyesters such as polyethylene terephthalate, or various elastomers, fluoropolymers such as ETFE, PEEK, polyimides and the like can be preferably used. In addition, the outer tube main body 31 may be made of a plurality of materials, and a reinforcing member such as a wire rod may be embedded therein.

The cutting portion 40 is a cutter that cuts and reduces the object such as a thrombus, a plaque, or a calcified lesion. Therefore, the "cut" means applying a force to the object in contact to make the object smaller. A method for applying the force in the cutting and a shape or a form of the object after the cutting are not limited. The cutting portion 40 has strength to cut the above-described object. The cutting portion 40 is fixed to the distal portion of the drive tube 21. The cutting portion 40 is a cylinder that protrudes toward the distal side with respect to the drive tube 21. A sharp blade 41 is provided at a distal end of the cutting portion 40. A shape of the blade 41 is not particularly limited. The cutting portion 40 may have a large number of minute abrasive grains instead of the blade 41.

A constituent material for the cutting portion 40 preferably has sufficient strength to cut a thrombus, and for example, stainless steel, titanium, diamond, ceramics, a shape memory alloy such as a nickel-titanium alloy, a cemented carbide such as tungsten carbide, an alloy (e.g., silver brazing filler metal) made of silver, copper, zinc, and the like, and high speed steel can be preferably used. The constituent material for the cutting portion 40 may be a resin such as engineering plastics such as polyether ether ketone (PEEK).

Figure 4A:
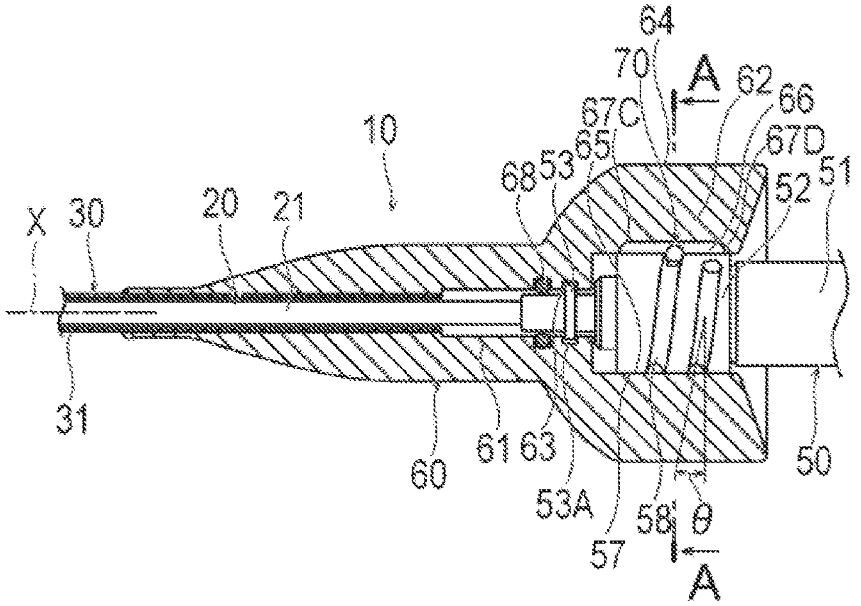
FIG. 4A is a cross-sectional view showing a second housing of a medical device according to a first embodiment.
Figure 4B:
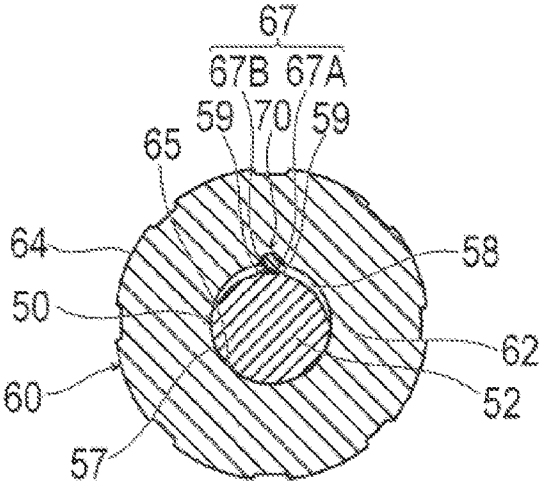
FIG. 4B is a cross-sectional view taken along a line A-A in FIG. 4A.

As shown in FIGS. 2, 4A and 4B, the moving member 70 is a member that limits relative rotation of the first housing 50 and the second housing 60 within a predetermined range. The moving member 70 is a sphere or ball disposed between the first housing 50 and the second housing 60. A shape of the moving member 70 is not limited to the sphere. The relative rotation of the first housing 50 and the second housing 60 includes a case where the first housing 50 stops and the second housing 60 rotates, a case where the second housing 60 stops and the first housing 50 rotates, and a case where both the first housing 50 and the second housing 60 rotate, but rotation speeds thereof are different.

The first housing 50 is located at a proximal portion of the medical device 10. The first housing 50 is a portion that is interlocked with the drive device 100 and receives a rotational driving force and an aspiration force from the drive device 100. The first housing 50 includes a housing main body 51 slidably connected to the second housing 60, an inner connecting portion 52, the joint 53, an aspiration port 54, a first seal portion 55 which may hereinafter be referred to as "first bearing," and a second seal portion 56 which may hereinafter be referred to as "second bearing." The first seal portion 55 may be located on an outer peripheral surface of the first bearing. The second seal portion 56 may be located on an outer peripheral surface of the second bearing.

The housing main body 51 includes an internal space 51A through which the drive tube 21 rotatably penetrates. The aspiration port 54 can be connected to an aspiration tube 131 of the drive device 100. The aspiration port 54 communicates with the internal space 51A. The proximal portion of the drive tube 21 penetrating the outer tube 30 and the second housing 60 is located in the internal space 51A. The lead-out portion 25 of the drive tube 21 is located in the internal space 51A. Therefore, a negative pressure acting on the aspiration port 54 from the aspiration tube 131 acts on the inside of the drive tube 21 from the lead-out portion 25. The first seal portion 55 that is in contact with an outer peripheral surface of the drive tube 21 is disposed on a proximal side of the housing main body 51. The second seal portion 56 that is in contact with the outer peripheral surface of the drive tube 21 is disposed on a distal side of the housing main body 51. The first seal portion 55 and the second seal portion 56 prevent the negative pressure in the internal space 51A from escaping. The first bearing and the second bearing cause rotation of the drive shaft 20 to be performed smoothly.

The joint 53 is a portion that rotatably interlocks the first housing 50 to the second housing 60. A ring-shaped joint convex portion 53A is formed on an outer peripheral surface of the joint 53. A third seal portion 68 that performs sealing between the first housing 50 and the second housing 60 is provided on a distal side with respect to the joint 53 of the first housing 50. The third seal portion 68 may be provided on the joint 53 or on a proximal side with respect to the joint 53.

The inner connecting portion 52 is disposed on the distal side of the housing main body 51 and fixed to the housing main body 51. The inner connecting portion 52 has a substantially cylindrical shape, and has a first facing surface 57 facing the second housing 60 on an outer peripheral surface thereof. The first facing surface 57 has a spiral first groove portion 58. A spiral angle θ, which is an angle formed by spiraling with respect to a plane orthogonal to a central axis of the spiraling, is more than 0° and less than 90°, preferably 1° to 45°, and more preferably 5° to 30°. A direction in which the first groove portion 58 draws the spiral is not particularly limited. An angle (hereinafter referred to as "extending angle") at which the first groove portion 58 extends along the circumferential surface thereof about the axis X of the drive shaft 20 is not particularly limited, and is, for example, 360° or more, preferably 720° or more, and more preferably 800° or more. When the extending angle of the first groove portion 58 is 360° or more, the second housing 60 can be rotated once with respect to the first housing 50, and the outer tube 30 fixed to the first housing 50 can be directed in all directions in a circumferential direction. When the extending angle of the first groove portion 58 is 720° or more, the second housing 60 can be rotated once in both directions (i.e., both clockwise and counterclockwise directions when viewed from the proximal side or the distal side) of a rotation direction with respect to the first housing 50. When the extending angle of the first groove portion 58 is 800° or more, the second housing 60 can be reliably rotated once in both directions of the rotation direction with respect to the first housing 50. When the extending angle of the first groove portion 58 is not too large, the guide wire is less likely to be entangled with a proximal side of the outer tube 30, and the outer tube 30 is less likely to be twisted.

The extending angle of the first groove portion 58 is not particularly limited, and is, for example, 1440° or less. The extending angle of the first groove portion 58 may be less than 360°. When the extending angle of the first groove portion 58 is less than 360°, the first groove portion 58 may extend on a plane orthogonal to the axis X without having the spiral angle θ (i.e., θ=0). If the extending angle of the first groove portion 58 is less than 360°, end portions of the first groove portion 58 do not communicate with each other even when the first groove portion 58 extends in the plane orthogonal to the axis X, and thus the end portions in the extending direction can be formed.

A depth of the first groove portion 58 is smaller than a diameter of the moving member 70, which is a sphere, and is, for example, about half the diameter of the moving member 70. A shape of a surface of the first groove portion 58 in a cross section orthogonal to the extending direction of the first groove portion 58 is an arc shape, and has a radius of curvature slightly larger than a radius of the moving member 70. Accordingly, the moving member 70 can smoothly move while rolling along the first groove portion 58. The cross-sectional shape of the surface of the first groove portion 58 is not limited to an arc shape.

Figure 11A:
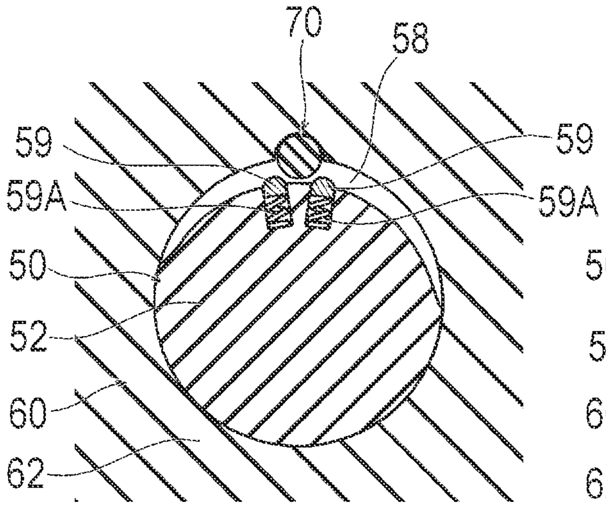
FIGS. 11A and 11B are cross-sectional views showing medical devices according to first and second modifications.
Figure 11B:
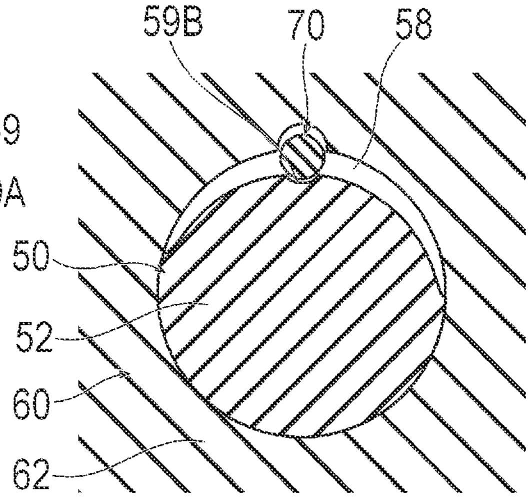

The first groove portion 58 has two protruding portions 59 arranged in the extending direction at substantially a center of the extending angle. The two protruding portions 59 has a height lower than the depth of the first groove portion 58. For example, the two protruding portions 59 has a height at which the moving member 70 moving along the first groove portion 58 can climb over while receiving resistance. A position between the two protruding portions 59 is an initial position at which the moving member 70 is disposed in an initial state before the medical device 10 is used. As in a first modification shown in FIG. 11A, the protruding portions 59 may be supported by elastic members 59A. Accordingly, the elastic members 59A contract when the moving member 70 passes over the protruding portions 59. Therefore, the moving member 70 can smoothly pass over the protruding portions 59. In addition, as in a second modification shown in FIG. 11B, the first groove portion 58 may have a concave portion 59B instead of the protruding portions 59. Since the concave portion 59B can hold the moving member 70, the concave portion 59B is effective as the initial position where the moving member 70 is disposed.

As shown in FIGS. 2, 4A and 4B, the second housing 60 is disposed on a distal side of the first housing 50. The second housing 60 is a portion that is rotated by fingers of an operator in order to rotate the outer tube 30. The second housing 60 includes a passage 61 through which the drive shaft 20 rotatably passes, and an outer connecting portion 62. The proximal portion of the outer tube 30 is interlocked with a distal portion of the passage 61 or the joint 53. In addition, a ring-shaped joint concave portion 63 into which the joint convex portion 53A of the first housing 50 is slidably fitted is formed on an inner peripheral surface of the passage 61. Accordingly, the second housing 60 is rotatable relative to the first housing 50, but is not movable relative to the first housing 50 in an axial direction.

The outer connecting portion 62 is formed in a substantially cylindrical shape and covers the inner connecting portion 52 of the first housing 50. An outer peripheral surface of the outer connecting portion 62 is an operation portion 64 that is touched by the operator to rotate the second housing 60. A second facing surface 65 facing the first facing surface 57 of the first housing 50 is formed on an inner peripheral surface of the outer connecting portion 62. A second groove portion 66 extending along the axis X of the drive shaft 20 is formed in the second facing surface 65. An extending direction of the second groove portion 66 is parallel to the axis X. However, the extending direction of the second groove portion 66 extending along the axis X of the drive shaft 20 is not necessarily parallel to the axis X.

The second groove portion 66 includes a contact portion 67 that can contact the moving member 70 and push the moving member 70. The contact portion 67 includes a first contact portion 67A that is an inner wall surface of the second groove portion 66 on a clockwise side, and a second contact portion 67B that is an inner wall surface of the second groove portion 66 on a counterclockwise side, when viewed from the proximal side. The first contact portion 67A and the second contact portion 67B are radially inward of a radially outermost position of the moving member 70 in a radial direction of the first housing 50 and the second housing 60. Accordingly, the first contact portion 67A and the second contact portion 67B can contact the moving member 70.

A depth of the second groove portion 66 is smaller than the diameter of the moving member 70, which is sphere-shaped, and is, for example, about half the diameter of the moving member 70. A shape of a surface of the second groove portion 66 in a cross section orthogonal to the extending direction of the second groove portion 66 is an arc shape, and has a radius of curvature slightly larger than the radius of the moving member 70. Accordingly, the moving member 70 can smoothly move while rolling along the first groove portion 58. The cross-sectional shape of the surface of the second groove portion 66 is not limited to an arc shape. A range in which the second groove portion 66 extends in a direction parallel to the axis X and a range in which the second groove portion 66 extends in the direction parallel to the axis X overlap each other. The moving member 70 is movable within the overlapping range. In the present embodiment, the entire first groove portion 58 is within the range in which the second groove portion 66 extends in the direction parallel to the axis X. The entire second groove portion 66 may be within a range in which the first groove portion 58 extends in the direction parallel to the axis X.

As constituent materials for the inner connecting portion 52, the outer connecting portion 62, and the moving member 70, for example, stainless steel, polyolefins such as polyethylene and polypropylene, polyamides, polyesters such as polycarbonates and polyethylene terephthalate, fluoropolymers such as an ethylene tetrafluoroethylene copolymer (ETFE), polyether ether ketone (PEEK), ABS (acrylonitrile, butadiene, and styrene copolymer), and polyimides can be preferably used.

Next, the drive device 100 will be described. As shown in FIG. 1, the drive device 100 includes a drive unit 120 that generates the rotational force and an aspiration unit 130 that generates an aspiration force. The drive unit 120 and the aspiration unit 130 are driven by an electric power supplied from an external power supply. The drive device 100 may include a battery that drives the drive unit 120 and the aspiration unit 130.

The drive unit 120 includes the rotary drive shaft 121 and a first motor 122 that rotates the rotary drive shaft 121. A rotation speed of the first motor 122 is not particularly limited, and is, for example, 5,000 to 200,000 rpm.

The aspiration unit 130 includes the aspiration tube 131, a pump 132, a second motor 133, and a waste liquid pack 135. The aspiration tube 131 can be connected to the aspiration port 54 of the medical device 10. The pump 132 is driven by the second motor 133 to apply the negative pressure to the aspiration tube 131. In addition, the pump 132 discharges a fluid aspirated through the aspiration tube 131 to the waste liquid pack 135.

A configuration of the drive device 100 is not limited to the example described above. For example, the rotational force and the aspiration force may be generated by separate devices.

Next, a method of using the medical device 10 according to the first embodiment will be described in a case in which a lesion area such as a thrombus or a calcified lesion in a blood vessel is removed and aspirated.

First, the operator inserts a guide wire W (see FIG. 3) into the blood vessel and causes the guide wire W to reach the vicinity of the lesion area. Next, the operator inserts a proximal end of the guide wire W into the guide wire lumen 33 of the medical device 10. Thereafter, the distal end of the medical device 10 is brought to the vicinity of the lesion area by using the guide wire W.

Figure 5A:
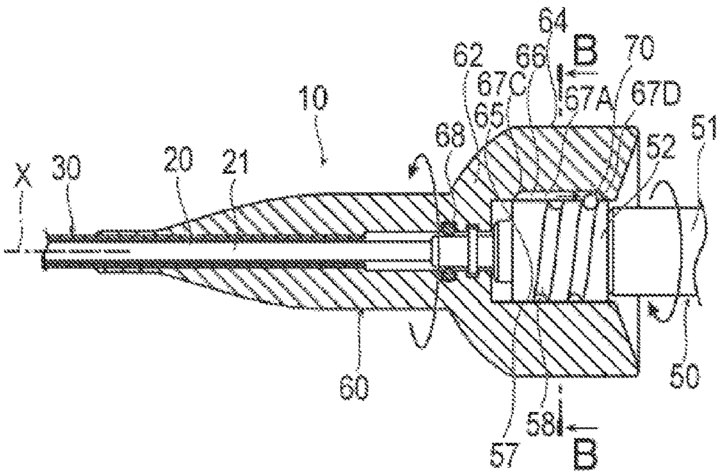
FIG. 5A depicts a state in which a second housing is rotated clockwise with respect to a first housing when viewed from a proximal side.
Figure 5B:
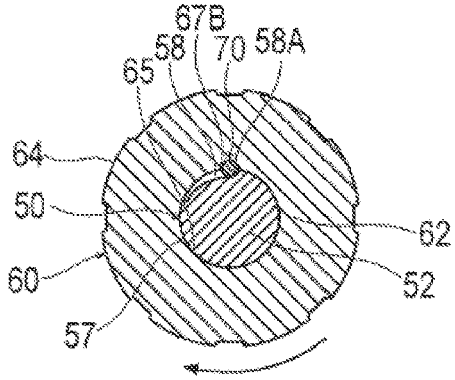
FIG. 5B is a cross-sectional view taken along a line B-B in FIG. 5A.

When the operator wants to change a position of the cutting portion 40 in a circumferential direction, the operator rotates the operation portion 64 of the second housing 60 while holding the first housing 50. For example, as shown in FIGS. 5A and 5B, when the second housing 60 rotates clockwise with respect to the first housing 50 when viewed from the proximal side, the outer tube 30 interlocked with the second housing 60 also rotates clockwise. Accordingly, a direction of the curved portion 34 of the outer tube 30 is changed, and the position of the cutting portion 40 can be changed.

When the second housing 60 rotates clockwise with respect to the first housing 50, the second contact portion 67B of the second groove portion 66 in the second housing 60 on the side (i.e., counterclockwise side) opposite to the rotation direction of the second housing 60 is pushed against the moving member 70 in the first groove portion 58. Accordingly, the moving member 70 is pushed by the contact portion 67 and moves in the first groove portion 58 in a circumferential direction. In addition, the moving member 70 moves in the second groove portion 66 toward the proximal side. At this time, since the moving member 70 is sphere-shaped, the moving member 70 can roll, and can smoothly move in the first groove portion 58 and the second groove portion 66. The moving member 70 moves in the first groove portion 58 and passes over the protruding portions 59 from the initial state in which the moving member 70 is held at a reference position between the two protruding portions 59. At this time, since the moving member 70 receives the resistance from the protruding portions 59, the operator can recognize the rotation of the first housing 50 from the initial state by a feeling (i.e., tactile sense) on his or her hand or fingers. In addition, in a case that a sound is emitted when the moving member 70 passes over the protruding portions 59, the operator can recognize the rotation of the first housing 50 from the initial state by the sound.

The second housing 60 and the outer tube 30 can rotate with respect to the first housing 50 until the moving member 70 pushed by the second contact portion 67B reaches an end portion 58A of the first groove portion 58 on a clockwise side in the extending direction. When the moving member 70 reaches the end portion 58A of the first groove portion 58 in the extending direction, the moving member 70 cannot move further in the circumferential direction. Accordingly, the moving member 70 is sandwiched between the second contact portion 67B of the second housing 60 and the end portion 58A of the first groove portion 58 in the extending direction. Therefore, the second housing 60 is restricted from further rotating in the clockwise direction with respect to the first housing 50 when viewed from the proximal side.

Figure 6A:
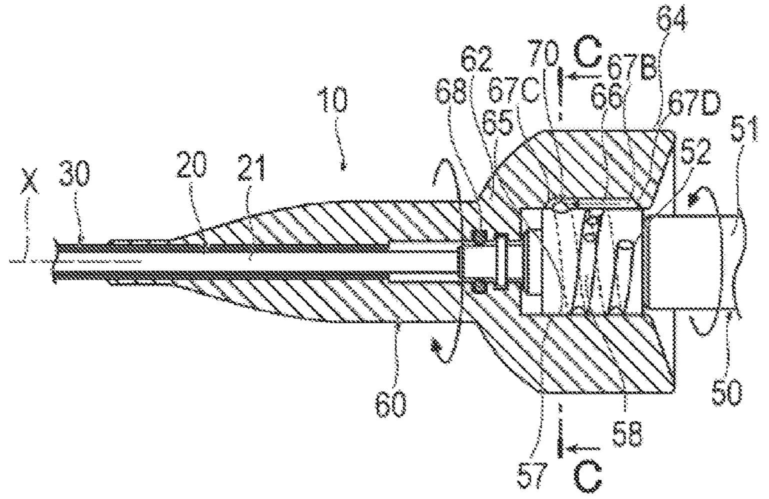
FIG. 6A depicts a state in which a second housing is rotated counterclockwise with respect to a first housing when viewed from the proximal side.
Figure 6B:
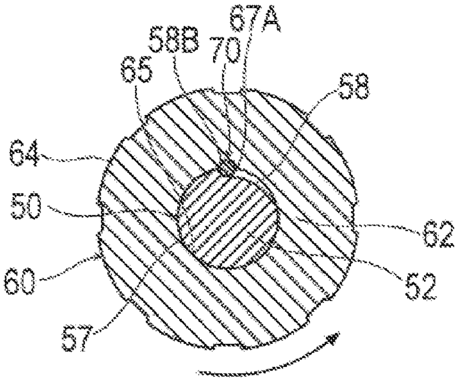
FIG. 6B is a cross-sectional view taken along a line C-C in FIG. 6A.

In addition, for example, as shown in FIGS. 6A and 6B, when the second housing 60 rotates counterclockwise with respect to the first housing 50 when viewed from the proximal side, the outer tube 30 interlocked with the second housing 60 also rotates counterclockwise. Accordingly, the direction of the curved portion 34 of the outer tube 30 is changed, and the position of the cutting portion 40 can be changed.

When the second housing 60 rotates counterclockwise with respect to the first housing 50, the first contact portion 67A of the second groove portion 66 formed in the second housing 60 on the side (clockwise side) opposite to the rotation direction of the second housing 60 is pushed against the moving member 70 in the first groove portion 58. Accordingly, the moving member 70 is pushed by the contact portion 67 and moves in the first groove portion in the circumferential direction. In addition, the moving member 70 moves in the second groove portion 66 toward the distal side. At this time, since the moving member 70 is sphere-shaped, the moving member 70 can roll, and can smoothly move in the first groove portion 58 and the second groove portion 66. The moving member 70 moves in the first groove portion 58 and passes over the protruding portions 59 from the initial state in which the moving member 70 is held at the reference position between the two protruding portions 59. At this time, since the moving member 70 receives the resistance from the protruding portions 59, the operator can recognize the rotation of the first housing 50 from the initial state by the feeling (tactile sense) on the hand or the fingers. In addition, in a case that the sound is emitted when the moving member 70 passes over the protruding portions 59, the operator can recognize the rotation of the first housing 50 from the initial state by the sound. The second housing 60 and the outer tube 30 can rotate with respect to the first housing 50 until the moving member 70 pushed by the first contact portion 67A reaches an end 58B of the first groove portion 58 on a counterclockwise side in the extending direction. When the moving member 70 reaches the end 58B of the first groove portion 58 in the extending direction, the moving member 70 cannot move further in the circumferential direction. Accordingly, the moving member 70 is sandwiched between the first contact portion 67A of the second housing 60 and the end 58B of the first groove portion 58 in the extending direction. Therefore, the second housing 60 is restricted from further rotating in the counterclockwise direction with respect to the first housing 50 when viewed from the proximal side.

When the second housing 60 is restricted from rotating with respect to the first housing 50, the guide wire lumen 33 is prevented from being entangled with the outer tube 30. In addition, the outer tube 30 is prevented from being twisted until the outer tube 30 is damaged.

Next, the operator connects the medical device 10 to the drive device 100 as shown in FIG. 2. Accordingly, the rotary drive shaft 121 is connected to the rotary input portion 24. In addition, the aspiration tube 131 is connected to the aspiration port 54. Thereafter, the operator operates the drive device 100. Accordingly, rotation of the rotary drive shaft 121 and aspiration of the aspiration tube 131 are started. The rotary drive shaft 121 rotates the rotary input portion 24. Accordingly, the drive shaft 20 fixed to the rotary input portion 24 and the cutting portion 40 are rotated. The rotating cutting portion 40 cuts the lesion area in the blood vessel.

The aspiration tube 131 applies the negative pressure to the internal space 51A via the aspiration port 54. Therefore, the negative pressure is applied on the aspiration lumen 22 of the drive shaft 20 through the proximal opening portion 25 located in the internal space 51A. Therefore, as shown in FIG. 3, the lesion area cut by the blade 41 of the cutting portion 40 becomes debris and moves inside the cutting portion 40 toward the proximal side. The debris is aspirated into the aspiration lumen 22 through the distal opening portion 26 of the drive shaft 20.

When the drive shaft 20 rotates, the outer tube 30 housing the drive shaft 20 receives the rotational force due to a frictional force from the drive shaft 20. Accordingly, the outer tube 30 and the second housing 60 interlocked with the outer tube 30 may rotate relative to the first housing 50. However, as aforementioned, the second housing 60 is restricted from rotating by a predetermined angle or more with respect to the first housing 50 by the moving member 70 accommodated in the first groove portion 58 and the second groove portion 66. Therefore, since the outer tube 30 does not rotate more than necessary even when receiving the rotational force from the drive shaft 20, the guide wire W passing through the guide wire lumen 33 is prevented from being entangled with the outer tube 30. In addition, since the outer tube 30 does not rotate more than necessary even when receiving the rotational force from the drive shaft 20, the outer tube 30 is prevented from being twisted until the outer tube 30 is damaged.

In addition, when the drive shaft 20 and the cutting portion 40 are rotating, the operator can arbitrarily change the position of the cutting portion 40 in the circumferential direction by rotating the operation portion 64 with the fingers or the hand. Therefore, a position to be cut by the cutting portion 40 can be easily adjusted with high accuracy.

The debris aspirated into the aspiration lumen 22 reaches the pump 132 through the lead-out portion 25, the internal space 51A, and the aspiration tube 131. The debris that has reached the pump 132 is discharged to the waste liquid pack 135 as shown in FIG. 1. After the cutting of the lesion area and the aspiration of the debris are completed, the operator stops the operation of the drive device 100. Accordingly, the rotation of the drive shaft 20 is stopped, and the aspiration of the pump 132 is stopped. Therefore, the cutting by the cutting portion 40 and the discharge of the debris are stopped. Thereafter, the operator removes the medical device 10 from the blood vessel and completes the procedure.

As described above, the medical device 10 according to the first embodiment is the medical device 10 that removes an object in the body lumen. The medical device includes: the drive shaft 20 that is rotatable; the outer tube 30 that rotatably accommodates the drive shaft 20; the cutting portion 40 that is interlocked with a distal portion of the drive shaft 20 and cuts the object; the first housing 50 that rotatably accommodates the drive shaft 20 and has the first facing surface 57 on an outer peripheral surface thereof; the second housing 60 that has the second facing surface 65 facing the first facing surface and is interlocked with the proximal portion of the outer tube 30; and the moving member 70 that is located between the first facing surface 57 and the second facing surface 65, in which the first groove portion 58 is formed in the first facing surface 57 or the second facing surface 65 in the circumferential direction, the moving member 70 is accommodated in the first groove portion 58, a part of the moving member 70 protrudes from the first groove portion 58, the first facing surface 57 or the second facing surface 65 facing the first groove portion 58 includes the contact portion 67 that is formed along the axis X of the drive shaft 20 and is attachable to the moving member 70, the second housing 60 is rotatable with respect to the first housing 50 about the axis X of the drive shaft 20, and the second housing 60 is restricted from rotating with respect to the first housing 50 by the moving member 70 contacting the end portions 58A, 58B of the first groove portion 58 or end portions 67C, 67D of the contact portion 67.

The contact portion 67 along the axis X of the drive shaft 20 means the contact portion 67 formed to have a direction component parallel to the axis X of the drive shaft 20. Therefore, the contact portion 67 along the axis X of the drive shaft 20 is not limited to a case where the contact portion 67 is parallel to the axis X of the drive shaft 20 as long as the contact portion 67 is not perpendicular to the axis X of the drive shaft 20. That is, even if the contact portion 67 is inclined with respect to the axis X of the drive shaft 20, the contact portion 67 has a direction component parallel to the axis X of the drive shaft 20. The end portions 58A and 58B of the first groove portion 58 are a start point and an end point of the first groove portion 58 in the extending direction. Alternatively, the end portions of the first groove portion 58 may be walls disposed between the start point and the end point of the first groove portion 58. The end portions 67C and 67D of the contact portion 67 are a distal surface and a proximal surface of the contact portion 67. Alternatively, the end portions of the contact portion 67 may be walls disposed between the distal surface and the proximal surface of the contact portion 67.

In the medical device 10 configured as described above, the second housing 60 is rotatable with respect to the first housing 50 until the moving member 70 reaches the end portions of the first groove portion 58 in the extending direction or the end portions of the contact portion 67 in the extending direction. Further, the second housing 60 is restricted from rotating with respect to the first housing 50 by the moving member 70 contacting the end portions of the first groove portion 58 in the extending direction or the end portions of the contact portion 67 in the extending direction. Therefore, a rotation amount of the outer tube 30 that rotatably accommodates the drive shaft 20 that drives the cutting portion 40 can be limited to a predetermined range. Therefore, it is possible to prevent the outer tube 30 from being twisted until the outer tube 30 is broken due to excessive rotation of the outer tube 30. In addition, it is possible to prevent the outer tube 30 from being entangled with the guide wire W or the like due to the excessive rotation of the outer tube 30.

The first groove portion 58 includes the protruding portions 59 or the concave portion 59B. Accordingly, the protruding portions 59 or the concave portion 59B can prevent the movement of the moving member 70 in the first groove portion 58, and can hold the moving member 70 at a predetermined position of the first groove portion 58. Therefore, the moving member 70 moves in the first groove portion 58 when pushed by the contact portion 67. Further, when the moving member 70 does not contact the contact portion 67, the moving member 70 is held at a position adjacent to the protruding portions 59 or in the concave portion 59B. In addition, the operator can recognize that the moving member 70 passes over the protruding portions 59 by the feeling (tactile sense) on the fingers or the hand or an auditory sense.

In addition, the first groove portion 58 includes at least two protruding portions 59. Accordingly, the moving member 70 can be well held between the two protruding portions 59. Therefore, when the moving member 70 is pushed by the contact portion 67, the moving member 70 passes over the protruding portions 59 and moves in the first groove portion 58. Further, when the moving member 70 does not contact the contact portion 67, the moving member 70 is held between the two protruding portions 59.

In addition, the first groove portion 58 is formed in a spiral shape in the second facing surface 65. Accordingly, the first groove portion 58 can be formed in a range of 360° or more when viewed from the proximal side or the distal side). Therefore, the outer tube 30 is rotatable by 360° or more with respect to the first housing 50.

In addition, the second groove portion 66 is formed in the second facing surface 65 facing the first groove portion 58, and the contact portion 67 is the inner wall surface of the second groove portion 66. Accordingly, when the outer tube 30 and the second housing 60 rotate with respect to the first housing 50, the second groove portion can contact the moving member 70 in any rotation direction. Therefore, the rotation amount of the outer tube 30 interlocked with the second housing 60 with respect to the first housing 50 can be limited to a predetermined range in any rotation direction.

Second Embodiment

Figure 7A:
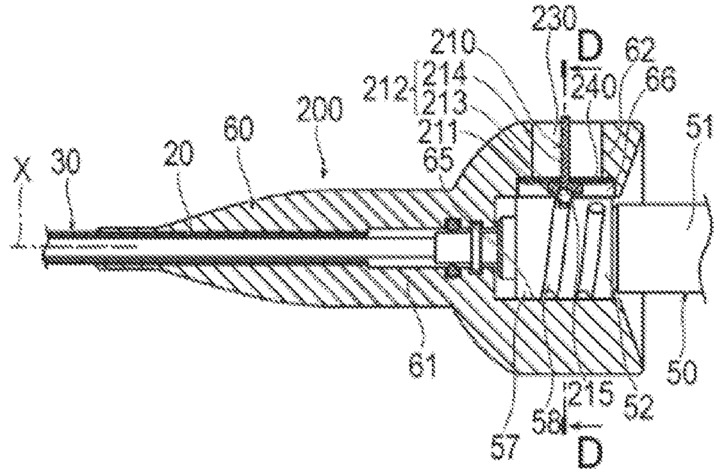
FIG. 7A is a cross-sectional view showing a second housing of a medical device according to a second embodiment.
Figure 7B:
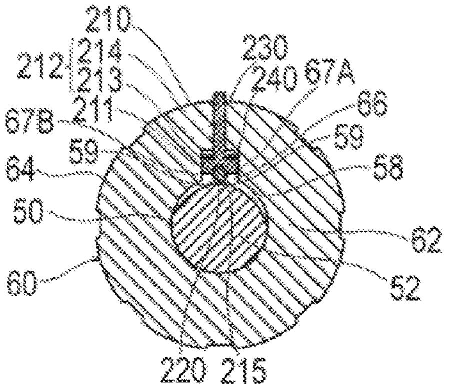
FIG. 7B is a cross-sectional view taken along a line D-D in FIG. 7A.

As shown in FIGS. 7A and 7B, a medical device 200 according to a second embodiment is different from the first embodiment in a structure of a moving member 210. The parts having same functions as those in the first embodiment are denoted by the same reference numerals, and descriptions thereof are omitted.

The first groove portion 58 of the first housing 50 has, between the two protruding portions 59, a second protruding portion 220 protruding at a height lower than the protruding portions 59. The second housing 60 includes a through-hole 230 extending radially outward from the second groove portion 66. The through-hole 230 penetrates to an outer surface of the second housing 60. The through-hole 230 is formed in a slit shape elongated in a direction along the axis X. A biasing member 240 that biases the moving member 210 toward the first facing surface 57 is disposed in the second groove portion 66 of the second housing 60. The biasing member 240 is, for example, a plate spring, and may be a coil spring or a high elastic modulus material such as rubber or elastomer. The biasing member 240 is slidable with the moving member 210, and does not limit the movement of the moving member 210 in the extending direction of the first groove portion 58.

The moving member 210 includes a main member 211 having a spherical shape and disposed in the first groove portion 58, and an auxiliary member 212 disposed in the second groove portion 66 and the through-hole 230. The auxiliary member 212 includes an inner auxiliary portion 213 disposed in the second groove portion 66 and an outer auxiliary portion 214 disposed in the through-hole 230. The inner auxiliary portion 213 is movable in the extending direction of the second groove portion 66. In the inner auxiliary portion 213, a holding hole 215 that holds the main member 211 is formed on a surface facing the first facing surface 57. The holding hole 215 is formed by a substantially hemispherical surface having a radius slightly larger than a radius of the main member 211. The outer auxiliary portion 214 is formed integrally with the inner auxiliary portion 213. The outer auxiliary portion 214 passes through the through-hole 230 and extends to the vicinity of the outer surface of the second housing 60 on an outer side in a radial direction.

When the main member 211 is located at the second protruding portion 220 which is a reference position sandwiched between the two protruding portions 59, the moving member 210 protrudes outward in the radial direction as a whole while being biased by the biasing member 240. Accordingly, a radially outer portion of the outer auxiliary portion 214 passes through the through-hole 230 and protrudes outward from the outer surface of the second housing 60. Therefore, the operator can easily recognize that the main member 211 is disposed at the reference position.

Figure 8A:
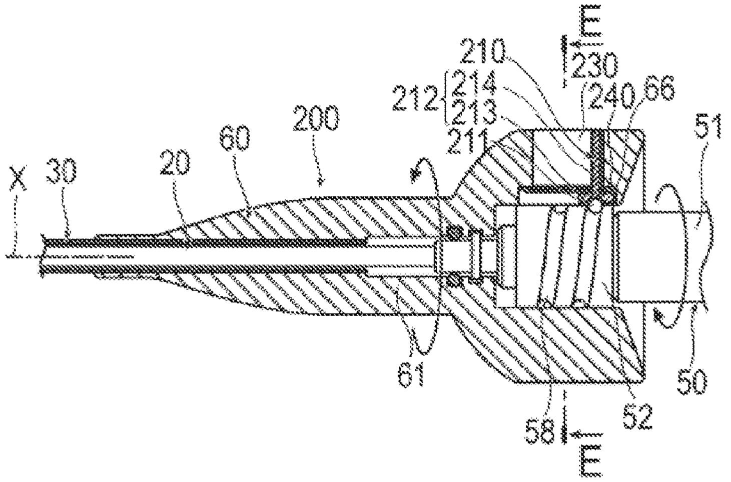
FIG. 8A depicts a state in which a second housing is rotated clockwise with respect to a first housing when viewed from the proximal side.
Figure 8B:
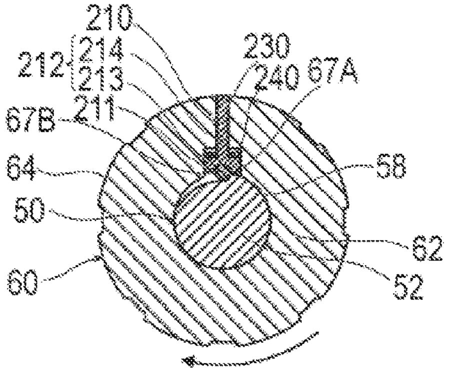
FIG. 8B is a cross-sectional view taken along a line E-E in FIG. 8A.

As shown in FIGS. 8A and 8B, when the main member 211 moves from the reference position and passes over any of the protruding portions 59, the main member 211 is disposed at a lower position different from the protruding portions 59 and the second protruding portion 220 of the first groove portion 58. Accordingly, the moving member 210 is biased toward the first facing surface 57 by the biasing member 240 and moves inward in the radial direction as a whole. Therefore, the radially outer portion of the outer auxiliary portion 214 is disposed at a position not protruding outward from the outer surface of the second housing 60. That is, the radially outer portion of the outer auxiliary portion 214 is disposed at substantially the same height as the outer surface of the second housing 60, or is disposed lower than the outer surface of the second housing 60. Accordingly, the operator can easily recognize that the second housing 60 and the outer tube 30 rotate with respect to the first housing 50 and the main member 211 moves from the reference position.

The radially outer portion of the outer auxiliary portion 214 may be disposed at substantially the same height as the outer surface of the second housing 60 when the main member 211 is disposed at the reference position, and may be disposed lower than the outer surface of the second housing 60 when the main member 211 moves from the reference position. In addition, the first groove portion 58 may include the concave portion 59B at the reference position. Accordingly, when the main member 211 is located at the reference position, the radially outer portion of the outer auxiliary portion 214 is located at substantially the same height as the outer surface of the second housing 60 or lower than the outer surface of the second housing 60. Further, when the main member 211 moves from the reference position, the radially outer portion of the outer auxiliary portion 214 may protrude from the outer surface of the second housing 60 or may be disposed at substantially the same height as the outer surface of the second housing 60.

As described above, in the medical device 200 according to the second embodiment, the first facing surface 57 is formed on the outer peripheral surface of the first housing 50, the second facing surface 65 is formed on an inner peripheral surface of the second housing 60, the second housing 60 includes the through-hole 230 extending radially outward from the second groove portion and penetrating to the outer surface of the second housing 60, and the moving member 210 includes the auxiliary member 212 disposed in the through-hole 230 and movable inside the through-hole 230. Accordingly, the operator can recognize the auxiliary member 212 by visual sense or tactile sense. Therefore, the operator can easily recognize that the moving member 210 passes over the protruding portions 59 or the concave portion 59B. If the protruding portions 59 or the concave portion 59B is formed in the first groove portion 58, the operator can easily recognize a depth of the auxiliary member 212 in the through-hole 230 and a protruding amount from the through-hole 230 by the visual sense or the tactile sense.

In addition, the medical device 200 includes the biasing member 240 that is disposed in the second groove portion 66 and biases the moving member 210. Accordingly, the moving member 210 can be pressed against the first groove portion 58 by the biasing member 240. Therefore, the moving member 210 is disposed at an appropriate position in the first groove portion 58, and easily moves along the first groove portion 58. In addition, the moving member 210 is biased by the biasing member 240 to move in a radial direction of the first housing 50 in accordance with a depth of the first groove portion 58. Therefore, the position (i.e., depth or protruding amount) of the auxiliary member 212 disposed in the through-hole 230 can be reliably changed according to a shape of the first groove portion 58. Therefore, for example, the operator can easily and accurately recognize that the moving member 210 passes over the protruding portions 59 or the concave portion 59B.

Third Embodiment

Figure 9A:
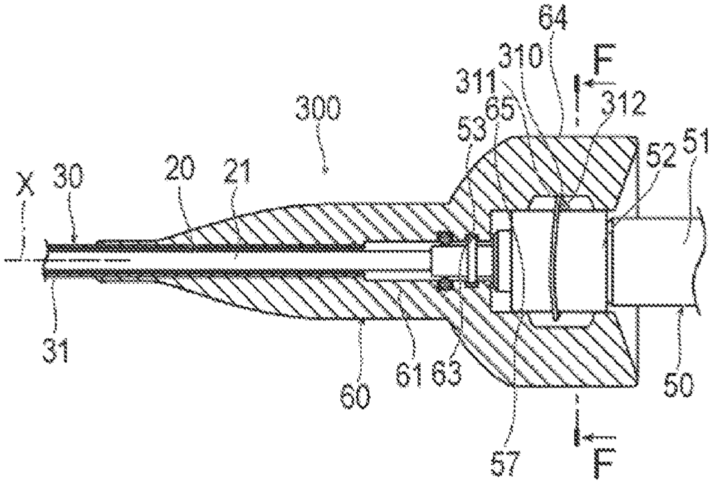
FIG. 9A is a cross-sectional view showing a second housing of a medical device according to a third embodiment.
Figure 9B:
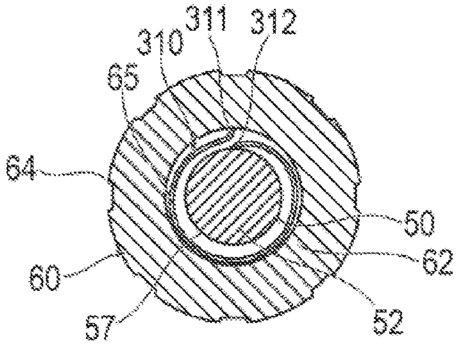
FIG. 9B is a cross-sectional view taken along a line F-F in FIG. 9A.

As shown in FIGS. 9A and 9B, a medical device 300 according to a third embodiment is different from the medical device 10 according to the first embodiment in that a limiting wire 310 is provided. The parts having same functions as those in the first embodiment are denoted by the same reference numerals, and descriptions thereof are omitted.

The first facing surface 57 of the first housing 50 and the second facing surface 65 of the second housing 60 are disposed apart from each other. The limiting wire 310 is a flexible wire, and includes a first interlock portion 311 and a second interlock portion 312. The first interlock portion 311 is interlocked with the first facing surface 57, and the second interlock portion 312 is interlocked with the second facing surface 65. In an initial state in which the first interlock portion 311 and the second interlock portion 312 are close to each other, the limiting wire 310 is loose.

When the second housing 60 rotates clockwise or counterclockwise relative to the first housing 50 as viewed from the proximal side, the second housing 60 is rotatable until the limiting wire 310 is not loose. When the limiting wire 310 is wound around the first facing surface 57 and is not loose, the second housing 60 is restricted from further rotating with respect to the first housing 50.

As described above, the medical device 300 according to the third embodiment is the medical device 300 that removes an object in a body lumen. The medical device 300 includes: the drive shaft 20 that is rotatable; the outer tube 30 that rotatably accommodates the drive shaft 20; the cutting portion 40 that is interlocked with the distal portion of the drive shaft 20 and cuts the object; the first housing 50 that rotatably accommodates the drive shaft 20; the second housing 60 that is interlocked with the proximal portion of the outer tube 30 and is rotatable with respect to the first housing 50 about an axis of the drive shaft 20; and the flexible limiting wire 310 that includes the first interlock portion 311 interlocked with the first housing 50 and the second interlock portion 312 interlocked with the second housing 60, in which the limiting wire 310 restricts the second housing 60 from rotating more than a predetermined rotation amount with respect to the first housing 50.

In the medical device 300 configured as described above, the second housing 60 is rotatable with respect to the first housing 50 until the limiting wire 310 is not loose. Further, since the limiting wire 310 is not loose, the rotation of the second housing 60 with respect to the first housing 50 is restricted. Therefore, a rotation amount of the outer tube 30 that rotatably accommodates the drive shaft 20 can be limited to a predetermined range. Therefore, it is possible to prevent the outer tube 30 from being twisted until the outer tube 30 is broken due to excessive rotation of the outer tube 30. In addition, it is possible to prevent the outer tube 30 from being entangled with the guide wire W or the like due to the excessive rotation of the outer tube 30.

Fourth Embodiment

Figure 10A:
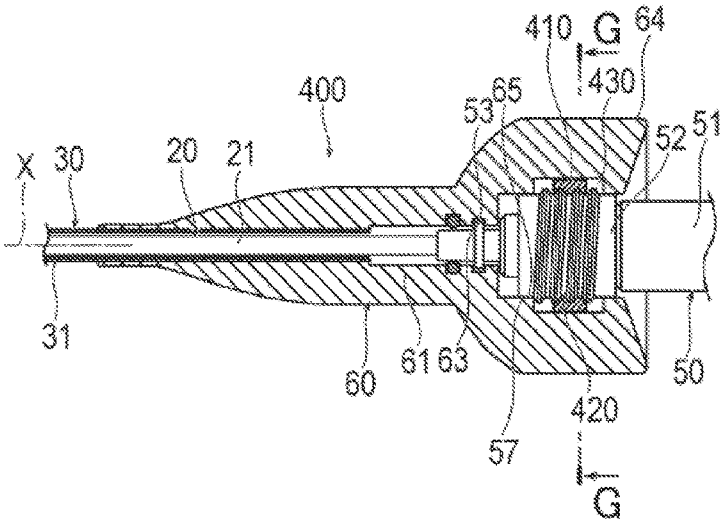
FIG. 10A is a cross-sectional view showing a second housing of a medical device according to a fourth embodiment.
Figure 10B:
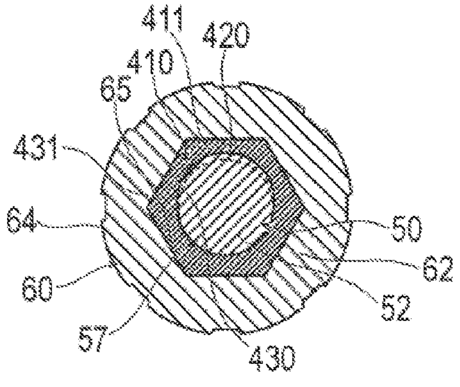
FIG. 10B is a cross-sectional view taken along a line G-G in FIG. 10A.

As shown in FIGS. 10A and 10B, a medical device 400 according to a fourth embodiment is different from the medical device 10 according to the first embodiment in that a moving member 410 has a nut shape and a first groove portion 420 has a bolt shape. The parts having same functions as those in the first embodiment are denoted by the same reference numerals, and descriptions thereof are omitted.

The first groove portion 420 is a bolt-shaped screw groove formed in the first facing surface 57 of the first housing 50. The moving member 410 is a nut that is screwed into the first groove portion 420. The moving member 410 is, for example, a hexagonal nut. The second facing surface 65 of the second housing 60 includes a second groove portion 430 in which the moving member 410 is slidable along the axis X. The second groove portion 430 includes a contact portion 431 that contacts an outer surface of the moving member 410 formed of six surfaces to restrict rotation of the moving member 410. The contact portion 431 does not restrict movement of the moving member 410 in a direction along the axis X.

When the second housing 60 rotates with respect to the first housing 50, the contact portion 431 of the second groove portion 430 formed in the second housing 60 contacts the moving member 410 accommodated in the first groove portion 420. Accordingly, the moving member 410 is pushed by the contact portion 431 and moves in a circumferential direction along the first groove portion 420. In addition, the moving member 410 moves toward the distal side or the proximal side along the second groove portion 430. The second housing 60 and the outer tube 30 can rotate with respect to the first housing 50 until the moving member 410 reaches an end portion of the first groove portion 420 in the extending direction or an end portion of the second groove portion 430 in the extending direction. When the moving member 410 reaches the end portion of the first groove portion 420 in the extending direction or the end portion of the second groove portion 430 in the extending direction, the moving member 410 cannot further move in the circumferential direction. Accordingly, the second housing 60 is restricted from further rotating with respect to the first housing 50.

This disclosure is not limited to the embodiments described above, and various modifications can be made by those skilled in the art within a scope of the technical idea of this disclosure. For example, the body lumen into which the medical devices 10, 200, 300, 400 are inserted is not limited to the blood vessel, and may be, for example, a vessel, a urinary duct, a bile duct, a fallopian tube, or a hepatic duct. Therefore, the object to be cut may not be a thrombus.

The width and/or the depth of the first groove portion 58 and/or the second groove portion 66 may decrease toward the end portions of the groove portion in the extending direction. Accordingly, the resistance when the first housing 50 is rotated with respect to the second housing 60 increases as the moving member 70 moves toward the end portions of the first groove portion 58 and/or the second groove portion 66 in the extending direction. Therefore, the operator can easily recognize how much the first housing 50 rotates with respect to the second housing 60 by the feeling of the fingers or the hand. In addition, as in the second embodiment, when the moving member 210 includes the auxiliary member 212 disposed in the through-hole 230, a degree of rotation can be recognized more easily and accurately by a position of the auxiliary member 212 in the through-hole 230 (i.e., depth in the through-hole 230 or protrusion amount from the through-hole 230).

In addition, in the first and second embodiments described above, the spiral first groove portion 58 is formed in the first facing surface 57 which is the outer peripheral surface of the first housing 50, and the second groove portion 66 is formed in the second facing surface 65 which is the inner peripheral surface of the second housing 60. However, the first groove portion 58 may be formed in the second facing surface 65, and the second groove portion 66 may be formed in the first facing surface 57. In addition, in the first and second embodiments, the first facing surface 57 is formed on the outer peripheral surface of the first housing 50, and the second facing surface 65 is formed on the inner peripheral surface of the second housing 60. However, the first facing surface 57 may be formed on an inner peripheral surface of the first housing 50, and the second facing surface 65 may be formed on an outer peripheral surface of the second housing 60. In such a case, the second facing surface 65 of the second housing 60 is disposed inside the first housing 50. Therefore, the portion of the second housing 60 to be rotated by the fingers is formed at a portion different from the portion in which the second facing surface 65 is formed.

In addition, in the second embodiment, the main member 211 and the auxiliary member 212 of the moving member 70 may be formed as an integrated member. In such a case, the main member 211 does not rotate with respect to the auxiliary member 212.

In addition, the biasing member 240 applied to the second embodiment may be disposed in the first groove portion 58 instead of the second groove portion 66, so as to bias the moving member 70 toward the second facing surface 65. In addition, the biasing member 240 may be disposed in both the first groove portion 58 and the second groove portion 66. In addition, the biasing member 240 may be interlocked with the moving member 210 and be movable together with the moving member 210. In addition, the biasing member 240 may be applied to the first and fourth embodiments.

In addition, the medical devices 10, 200, 300, 400 and the drive device 100 may be integrally configured.

What is claimed is:

1. A medical device that removes an object in a body lumen, the medical device comprising:
- a rotatable drive shaft;
- an outer tube that accommodates the drive shaft and is rotatable independent of the drive shaft;
- a cutter attached to a distal portion of the drive shaft and by which the object is cut;
- a first housing that accommodates a proximal portion of the drive shaft and has an outer surface including a first groove that extends around a rotation axis of the drive shaft;
- a second housing that is interlocked with a proximal portion of the outer tube and rotatable around the first housing, the second housing having an inner surface that faces the outer surface of the first housing and includes a second groove that extends along the rotation axis of the drive shaft; and
- a ball that fits into the first and second grooves and is movable along both the first and second grooves concurrently according to rotation of the second housing, wherein
- the first housing includes at least one of a protruding portion and a concave portion in the first groove corresponding to an initial position of the ball.

2. The medical device according to claim 1, wherein the second housing is restricted from rotating with respect to the first housing when the ball reaches either a distal end of the first groove or the second groove or a proximal end of the first groove or the second groove.

3. A medical device that removes an object in a body lumen, the medical device comprising:
- a rotatable drive shaft;
- an outer tube that accommodates the drive shaft and is rotatable independent of the drive shaft;
- a cutter attached to a distal portion of the drive shaft and by which the object is cut;
- a first housing that accommodates a proximal portion of the drive shaft and has an outer surface including a first groove that extends around a rotation axis of the drive shaft;
- a second housing that is interlocked with a proximal portion of the outer tube and rotatable around the first housing, the second housing having an inner surface that faces the outer surface of the first housing and includes a second groove that extends along the rotation axis of the drive shaft; and
- a ball that fits into the first and second grooves and is movable along both the first and second grooves concurrently according to rotation of the second housing, wherein
- the first groove is formed in a spiral shape.

4. The medical device according to claim 3, wherein the first groove extends along the outer surface of the first housing such that the second housing is rotatable around the first housing by 360 degrees or more.

5. The medical device according to claim 4, wherein the second housing is rotatable around the first housing by 800 degrees or more.

6. The medical device according to claim 1, wherein the second housing includes:
- a through-hole extending radially outward from the second groove to an outer surface of the second housing, and
- an auxiliary member movable along the through-hole as the ball moves along the second groove.

7. The medical device according to claim 6, wherein
- the first housing includes a protruding portion in the first groove, and
- the auxiliary member protrudes from the outer surface of the second housing when the ball is on the protruding portion.

8. The medical device according to claim 1, wherein a width of at least one of the first and second grooves decreases toward distal and proximal ends thereof.

9. The medical device according to claim 1, wherein a depth of at least one of the first and second grooves decreases toward distal and proximal ends thereof.

10. The medical device according to claim 9, wherein and
- a diameter of the ball is greater than the depth of at least one of the first and second grooves.

11. The medical device according to claim 1, further comprising:
- a biasing member disposed in the second groove to bias the ball toward the first housing.

12. The medical device according to claim 1, wherein
- the first groove is formed along a first part of the outer surface of the first housing, and
- when viewed in a direction perpendicular to the rotation axis of the drive shaft, the second groove has a length that corresponds to a length of the first part in a direction parallel to the rotation axis.

13. A medical device that removes an object in a body lumen, the medical device comprising:
- a rotatable drive shaft;
- an outer tube that accommodates the drive shaft and is rotatable independent of the drive shaft;
- a cutter attached to a distal portion of the drive shaft and by which the object is cut;
- a first housing that accommodates a proximal portion of the drive shaft and has an outer surface including a first groove that extends around a rotation axis of the drive shaft;
- a second housing that is interlocked with a proximal portion of the outer tube and rotatable around the first housing, the second housing having an inner surface that faces the outer surface of the first housing and includes a second groove that extends along the rotation axis of the drive shaft; and
- a ball that fits into the first and second grooves and is movable along the first and second grooves according to rotation of the second housing, wherein
- a depth of at least one of the first and second grooves decreases toward distal and proximal ends thereof.

14. The medical device according to claim 13, wherein
- a diameter of the ball is greater than the depth of at least one of the first and second grooves.

* * * * *